United States Patent [19]

Kelly

[11] 4,085,609
[45] Apr. 25, 1978

[54] DROPWEIGHT SAMPLE TESTER

[75] Inventor: John H. Kelly, Burlington, Canada

[73] Assignee: The Steel Company of Canada, Limited, Hamilton, Canada

[21] Appl. No.: 725,399

[22] Filed: Sep. 22, 1976

[30] Foreign Application Priority Data

Jul. 26, 1976  Canada ................... 257740

[51] Int. Cl.² ............................................. G01N 3/30
[52] U.S. Cl. ........................................ 73/101; 73/12
[58] Field of Search ............... 73/101, 87, 103, 12; 356/28; 324/175, 178; 250/238

[56] References Cited

U.S. PATENT DOCUMENTS

| 2,778,219 | 1/1957 | Wachter | 73/87 |
| 3,285,060 | 11/1966 | Pessen | 73/101 |
| 3,538,743 | 11/1970 | Glidden | 73/12 |

OTHER PUBLICATIONS

Journal of Applied Physics, Equipment to Measure the Energy Absorption of Films at High Strain Rates, vol. 28, #3, Mar., 1957, Spangler et al.

*Primary Examiner*—James J. Gill
*Assistant Examiner*—Anthony V. Ciarlante
*Attorney, Agent, or Firm*—Sim & McBurney

[57] ABSTRACT

This invention provides a process and apparatus for determining the energy absorbed by a test-piece of material during its fracture. The test-piece is supported horizontally between two separated anvils, and a dropweight is released from a position above the test-piece so that the same can be struck and fractured. Means are provided for determining, by measuring a determining characteristic of the motion of the dropweight after the test-piece has been fractured, the theoretical height from which the dropweight would have had to be released in order to have that post-fracture motion if the test-piece had not been in the way. The difference between this calculated theoretical height and the actual height of release, multiplied by the weight of the dropweight, provides a measure of the energy absorbed by the test-piece during its fracture.

1 Claim, 4 Drawing Figures

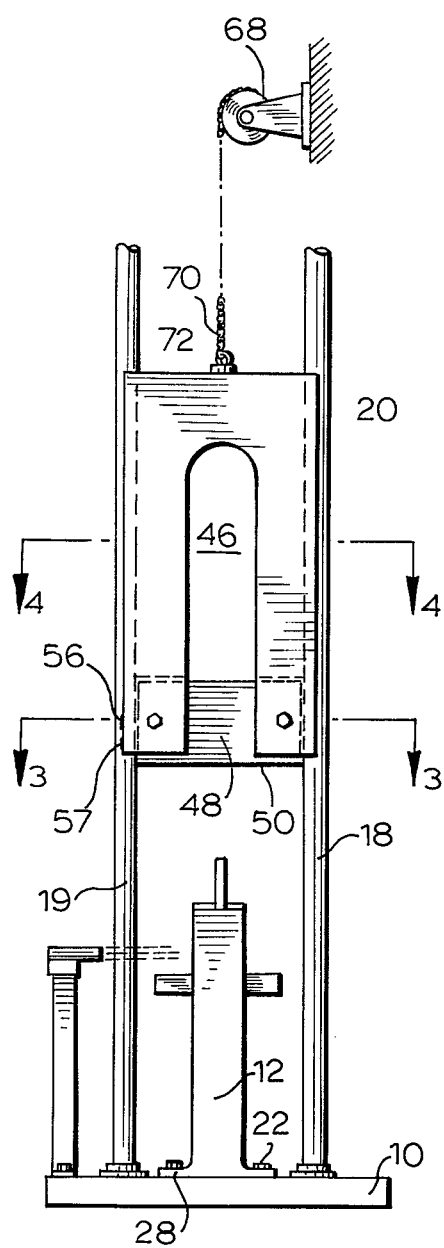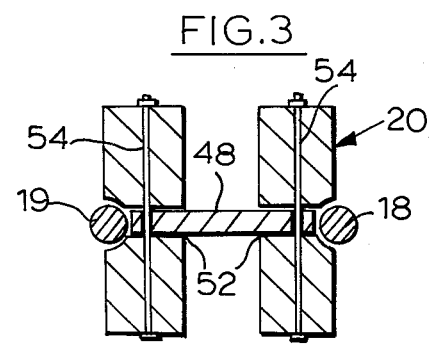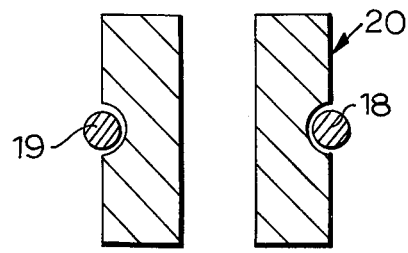

DROPWEIGHT SAMPLE TESTER

This invention relates generally to the area of materials-testing, and has to do particularly with a procedure and an apparatus useful for determining the energy absorbed in fracturing a test-piece.

Many methods are currently utilized in determining the amount of energy absorbed in the fracture of a test-sample, particularly in the area of specialty steels and steel alloys. One such test is called the Charpy test, in which a weight carried on a pendulum swings down from a raised position to strike the middle of a test-sample which is held at either end, the striking taking place at the bottom or "six o'clock" position in the movement of the pendulum. The energy potentially available in the pendulum in the initial raised position is determined by its height above the strike location, and whatever energy remains in the pendulum after fracturing the test-sample will cause the pendulum to swing further and rise along a certain arc which can be measured. The maximum height to which the weight rises after fracturing the test-sample is proportional to the energy remaining in the weight after the fracture of the test-sample, and the difference between this and the initial energy is that which is absorbed by the sample during fracture.

The Charpy test and procedures similar to it are limited to relatively low fracture energies and have further disadvantages related to the space required to permit the weight/pendulum combination to swing freely.

To accommodate larger energies, considerably larger pendulums would have to be built, but these are both costly and difficult to construct.

Fracture tests are used for other purposes than simply the determination of absorbed fracture energy. For example, much of the piping utilized for pipelines in the Arctic is manufactured by a helical seam-welding procedure, in which heavy steel plate with a thickness in the area of ½ inch to 1 inch (normally called "skelp") is helically coiled and advanced while being simultaneously welded as the edges come together, to form very large-diameter pipe capable of withstanding very high internal pressures.

Because pipelines so manufactured may undergo ambient temperatures as low as −100° F, it is desirable to know the nature of a fracture occurring in this material in the low temperature range. It is known that the brittleness of certain steels increases as the temperature drops, and it is of advantage to ensure that steel skelp of the kind proposed for use in Arctic pipelines will undergo ductile fracture to some extent, in order to avoid the risk that a crack or split at one portion of a highly pressurized pipeline in very cold conditions will not run rapidly along the pipeline due to the inability of the skelp to absorb energy at those temperatures.

In order to determine the nature of the fracture for such material, it is known to prepare elongated test samples with a notch about the middle of one longitudinal edge, to cool the sample down to a desired stipulated temperature, for example −100° F, to mount the sample between two firm supports such that the "V"-notch is downwardly, and then to drop a relatively heavy dropweight vertically down to strike the sample at the edge opposite the "V"-notch, thereby to cause a fracture to propagate through from the underlying "V"-notch to the edge which has been struck. An examination of the fracture surfaces will then allow the operator to determine whether the sample underwent ductile or brittle fracture.

It is an aspect of this invention to modify the last-mentioned procedure in order to allow a ready computation of the total energy absorbed by the test-sample during its fracture by the freely vertically falling dropweight.

Dropweight towers can be instrumented to measure the deceleration of a dropweight by attaching bonded wire strain gages or piezoelectric transducers to the striker bar (or suitably designed anvils). The attachment of shielded cables to the dropweight would create maintenance problems, however. The resonant vibrations within the dropweight (or the anvils) would tend to contribute unwanted signals during impact. Therefore, the latter approach is neither reliable nor accurate unless great expense and design effort is expended.

Where only a few samples are to be tested, as during an investigation of material properties, a cube of aluminum may be used. The remaining energy in the dropweight is used to deform the cube. The change in the dimensions of the cube is correlated with the known energy required to cause that deformation.

However, for repeated testing of a large number of samples, the use of aluminum cubes is not really a practical matter, and it is an aspect of this invention to provide a superior method of determining loss of energy by the dropweight during impact. It is also an aspect of this invention to obviate the difficulties and drawbacks mentioned previously in connection with the use of strain gages or piezoelectric transducers.

It is well understood that the total potential energy in the dropweight available to be applied to a sample is determined by multiplying the weight of the dropweight by the effective height of the dropweight above the test-piece. After the dropweight has struck and fractured the test-piece, some energy will remain in the dropweight as kinetic energy. In other words, the dropweight will be continuing to fall, and its speed at any given point when multiplied by it mass will give the instantaneous kinetic energy. The difference between these two energies (so long as both are referenced to the position of the test-piece) is a measure of the energy absorbed by the test-piece during fracture.

It is not practical for a number of reasons to actually measure the remaining kinetic energy in the dropweight after fracture by "catching" and absorbing the energy in some deceleration device like a shock absorber. When what is contemplated is to catch and decelerate a dropweight with a mass of 1200 pounds falling from 12 feet, even after some of that energy has been absorbed in the fracture of the test-piece, the strain placed on the device utilized to catch and decelerate the dropweight is very considerable, and a proposal to utilize that particular device as a sensitive instrument to determine the energy thus absorbed would immediately encounter problems of wear, distortion, oil leakage (in the case of an oil filled shock absorber), and simple fracture of the loaded portions.

In view of the foregoing problems and discussion, this invention proposes a novel and useful method of determining absorbed energy during facture.

Accordingly, this invention provides apparatus for determining the energy absorbed by an elongated test-piece of material during fracture thereof, comprising:

support means for supporting the test-piece during fracture including anvil means at either end of the test-piece;

a dropweight, vertical guide means for the dropweight, means for raising the dropweight along the guide means, and means for releasing the dropweight from a raised position directly above the test-piece to undergo substantial free-fall vertically after release, and means for measuring a determining characteristic of the motion of the dropweight after the test-piece has been fractured, the latter means including two retro-reflective areas affixed in vertically separated relation on the dropweight, a photoelectric beam projecting such that the retro-reflective areas pass sequentially into said beam, light-detecting means for sensing light reflected from said areas and for generating two time-separated electrical signals as the two areas pass sequentially into the beam, and electronic period-counter means to measure the time elapsing between the two electrical signals, the dropweight being an integral mass of metal shaped to define two downwardly extending, laterally spaced-apart arms joined integrally together at the top thereby providing an internal slot extending upward from the bottom, the said guide means maintaining the dropweight in an orientation such that the test-piece is aligned with said internal slot, the dropweight including a striker bar supported horizontally across and at right-angles to said slot and said test-piece, whereby the striker bar contacts the test-piece substantially mid-way of each so that the fractured separated ends of the test-piece can pivot inwardly and into the slot above the striker bar, thus avoiding interference with the further downward free-fall of the dropweight, and means directly beneath the initial test-piece location for catching and decelerating the dropweight after fracture of the test-piece.

One embodiment of this invention is illustrated in the accompanying drawings, in which like numerals denote like parts throughout the several view, and in which:

FIG. 2 is an elevational view of the apparatus of FIG. 1; and

Figure 1:
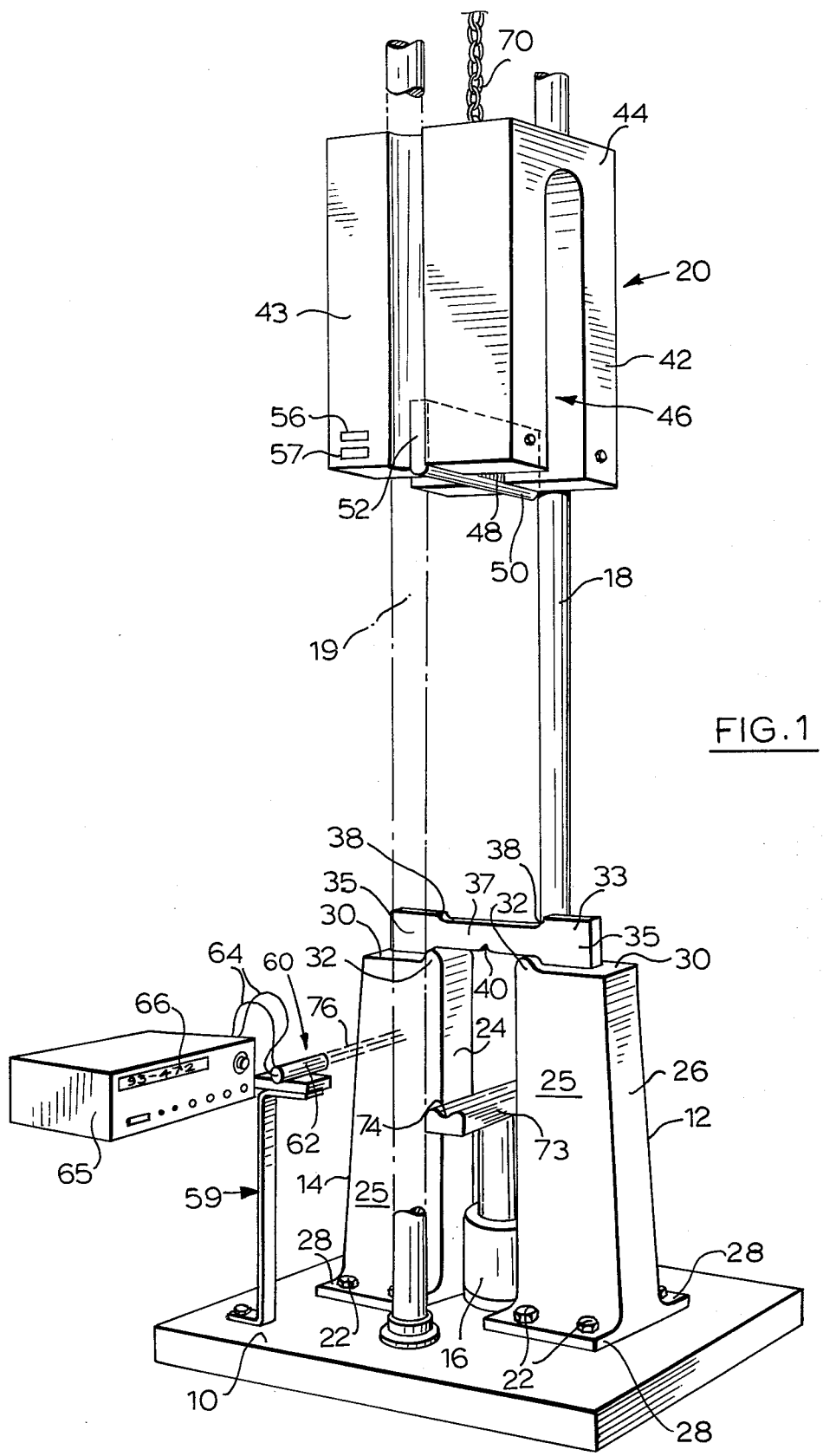
FIG. 1 is a perspective view of an apparatus embodying this invention.

FIGS. 3 and 4 are horizontal sectional views taken at the lines 3—3 and 4—4 respectively in FIG. 2.

Attention is directed first to FIG. 1 in which the apparatus of this invention is shown to include a base-pad 10 constituted by a concrete pad or the like, two upstanding anvils 12 and 14, a shock absorber 16, two vertical guide rails 18 and 19 and a dropweight 20.

The anvils 12 and 14 are securely anchored by steel bolts 22 to the base pad 10, the latter being substantially rectangular as illustrated. Each anvil 12, 14 has a substantially vertical inside face 24, vertical side walls 25, and a downwardly and outwardly sloping outer wall 26. Each anvil also is integral with outward flanges 28 at the bottom, through which the bolts 22 pass.

Each anvil 12, 14 has an upper face 30 which defines at its inside portion an upwardly extending protuberance or rib 32.

In FIG. 1 a typically-shaped test-piece 33 is illustrated in its position supported by the two anvils 12 and 14. The illustrated test-piece 33 includes two end portions 35, a central waisted portion 37, and transition radiuses 38 having substantially the same radius of curvature as the ribs 32 on the anvils 12 and 14. The test-piece 33 is typically machined from a piece of steel or steel alloy plate, called "skelp", and thus is relatively narrow and elongated. A transverse section taken through the waisted portion 37 would thus be a rectangle with a longer dimension perhaps 6 to 10 times as great as the smallest dimension (the thickness of the skelp). As illustrated in FIG. 1, the test-piece is positioned on the anvils 12 and 14 such that the original plane of the skelp from which the test-piece is machined lies vertically and passes through both anvils 12 and 14. The test-piece 33 is provided with a "V"-notch 40 centrally of its bottom edge in the waisted portion 37, the notch 40 being machined or impact-impressed.

It will thus be seen that the test-piece 33 is supported in the manner of a simple beam, with solid support under either end and the intention being that the fracturing load will be applied in the middle between the two support locations. This means that the fracturing impact will take place along the upper edge of the waisted portion 37, substantially directly opposite the "V"-notch 40, thus ensuring that a fracture will begin to propagate from the "V"-notch 40 and will extend through to the upper side to complete the fracturing of the test-piece.

The dropweight 20 has somewhat the shape of an upside-down tuning fork, this shape being evident in the view of FIG. 2. More particularly, the dropweight is preferably an integral mass of low-alloy steel in the normalized condition, shaped to define two downwardly extending, laterally spaced-apart arms 42 and 43 which are joined integrally together at the top 44. The two arms 42 and 43 thus define an internal slot 46 extending upwardly from the bottom, the slot being aligned with the test-piece 33. Extending across the bottom portion of the slot 46 is a striker bar 48 which is supported horizontally and which has a rounded striking edge 50.

Each of the arms 42 and 43 has an upwardly extending striker bar cavity 52, the two cavities 52 being aligned and being adapted to receive the striker bar 48 as seen in FIGS. 1 and 2. When in place, the striking edge 50 of the striker bar 48 projects downwardly below the lower surfaces of the arms 42 and 43. The cavities 52 are larger in lateral dimension than the width of the striker bar 48, and in the absence of some means for maintaining the striker bar in position, the striker bar would fall out of the cavities 52. In order to maintain the striker bar 48 in position, two elongated bolts 54 are provided, which pass through suitable bore holes in the arms 42 and 43 and simultaneously through oversized apertures in either end of the striker bar 48. This structure is clearly illustrated in FIG. 3. The heads of the bolts 54 are visible in FIGS. 1 and 2.

Affixed to the outer vertical surface of the arm 43 of the dropweight 20 are two rectro-reflective areas or tapes 56 and 57, these being positioned in vertical stacked relation, with the tape 56 being spaced a predetermined distance above the tape 57.

Affixed to the base pad 10 is a brace member 59 which extends upwardly and then rightwardly (as seen in FIG. 1) in a plane which passes to the viewer's side of the vertical rail 19 in FIG. 1, and which supports a photoelectric apparatus shown generally at 60. The photoelectric apparatus 60 includes a tubular projection and detection portion 62 in the far end of which (in FIG. 1) is located a standard light-emitting source and a photoelectric detection cell. In one typical arrangement, the source is provided concentrically around the detection cell. Wires 64 lead from the portion 62 to an electronic period counter 65 of conventional manufacture, which is adapted to display in window 66 the time elapsing between two sequential electrical signals or "blips" received from the photoelectric apparatus 60.

This apparatus also includes means for raising the dropweight 20 to a predetermined height and for releasing it for substantially free-fall guided by the rails 18 and 19. In the drawings, this means is illustrated to include a winch 68 and a lift chain 70. The lower end of the lift chain 70 is adapted to be releasably attached at the location 72 atop the dropweight 20. Electrical or air-operated means (not shown) may be provided for triggering the release of the chain 70 from the dropweight 20.

The operation of the apparatus illustrated in the figures is as follows. A test-piece is first machined to the desired shape and provided with a "V"-notch if the nature of the test calls for such a notch. If the purpose of the test is to determine fracture characteristics at Arctic temperatures, the test-piece is then subjected to a very low temperature environment to drop its temperature to the desired level, thus simulating Arctic conditions. The test-piece is then placed across the anvils 12 and 14 as illustrated in FIG. 1, it being understood that the dropweight 20 has previously been raised by the winch 68 to a predetermined height, ready for release. The method of this invention requires a close determination of the height of the dropweight above some reference point prior to release, the reference point being any suitable horizontal plane so long as the height of the reference plane with respect to the portion 62 of the photoelectric apparatus 60 is determinable.

The dropweight 20 is then released by disengaging the lower end of the chain 70 from the top of the dropweight 20, and the dropweight undergoes free-fall downwardly while guided by the rails 18 and 19.

The striker bar 48 contacts the test-piece 33 at approximately the mid-point of the uppermost edge of the waisted portion 37 thereof, and thus transmits the full force of the dropweight 20 against the test-piece at this point. It is assumed here that the kinetic energy in the dropweight 20 at the time of impact is more than sufficient to completely fracture the test-piece 33, with the actual fracture propagating upwardly through the test-piece from the notch 40.

As can be seen in FIGS. 1 and 2, the anvils 12 and 14 are narrow enough to be received within the slot 46 of the dropweight 20 as the dropweight descends further subsequent to fracturing the test-piece 33. Also, the two separated ends of the fractured test-piece 33 undergo inward and downward rotation under the urging of the striker bar 48, with the end portions 35 of the test-piece 33 rotating up into the slot 46 and thus not interfering with the further downward fall of the dropweight 20.

As is best seen in FIG. 1, the shock absorber 16 supports at its upper end a catch-rail 73 which is provided with a central elongated channel 74 exactly aligned with the lower striking edge 50 of the striker bar 48. The dropweight 20 thus falls downwardly until the striker bar 48 is received in the channel 74, whereupon the shock absorber 16 decelerates the dropweight 20 to a standstill by absorbing the remaining kinetic energy at the time of contact between the striker bar 48 and the catch-rail 73 of the shock absorber 16.

Before any contact between the striker bar 48 and the catch-rail 73, both of the retro-reflective tapes 56 and 57 pass downwardly sequentially through a light beam 76 projected horizontally by the portion 62 of the photoelectric apparatus 60, the direction of the beam projection being substantially perpendicular to the corresponding vertical side wall of the dropweight 20, i.e. the side wall against which the retro-reflective tapes 56 and 57 are located.

When the first retro-reflective tape 57 passes into the light beam 76, a reflected beam is directed back to the portion 62, which as mentioned previously is equipped with a photoelectric sensor capable of giving rise to an electric impulse proportional to the light beam intensity. Strictly speaking, the electrical impulse will be in the form of a very fast (though not instantaneous) increase in voltage, and the period counter 65 is adapted to initiate the counting procedure when this rapidly increasing voltage reaches a given threshold level.

When the first retro-reflective tape 57 passes downwardly out of the beam 76, the voltage generated in the portion 62 of the photoelectric apparatus 60 drops down below the threshold. This does not halt the counting however, as the period counter 65 is set is arrest the time-counting procedure only upon a next subsequent increase of the generated voltage to the same threshold as previously. This occurs as the uppermost retro-reflective tape 56 passes into the light beam 76, and when the aforementioned threshold is reached the period counter stops, and displays or otherwise registers the time which has elapsed. In one available period counter, the device is adapted to display the measured time in milliseconds, the value being given to the nearest hundredth of a millisecond.

The next step in the method accordingly to this invention is to utilize the displayed time lapse to determine the theoretical height from which the dropweight 20 would have had to be released in order to fall in the absence of the test-piece and produce the same time lapse between sequential passages of the retro-reflective tapes into the light beam as was actually measured. Naturally, this height will be lower than the actual height from which the dropweight was released prior to fracturing the test-piece, and the difference in heights, when multiplied by the weight of the dropweight, will yield the energy absorbed by the test-piece 33 during its fracture.

For reasons relating to set standards (particularly in North America) and to what has become common and well-known in the testing field, it is convenient to arrange the apparatus of this invention in such a way as to provide a plurality of different nominal kinetic energies available to fracture a test-piece when the striker bar 48 comes into contact with the piece to be fractured. For example, two dropweight masses could be utilized, at 300 lbs and 1200 lbs respectively, and either of these dropweights could be released from any of three initial heights above the test-piece. These heights may be 4 feet, 8 feet, and 12 feet. Thus, the two available dropweight masses and the three available dropheights would allow six possible kinetic energy ranges, namely 1200, 2400, 3600, 4800, 9600 and 14,400 ft. lb.

From the viewpoint of obtaining the greatest accuracy in determining the amount of energy absorbed by a given test-piece during fracture, it is desirable to choose a combination of dropweight mass and dropheight which will yield a kinetic energy at impact which is sufficient to fracture the test specimen, but which exceeds the absorbed fracture energy by the least possible amount. To illustrate why this is important, we shall consider an apparatus in which the lower edges of the retro-reflective tapes 56 and 57 are set exactly 2.00 inches apart, and in which the exact mass of the larger dropweight is 1156 lbs. We shall drop the dropweight from a height of 8.74 feet. If the test specimen only absorbed 855 ft. lb. of energy, then the measured period generated by the period counter 65 will be in the area of 7.31 milliseconds, which can be utilized mathematically to calculate a theoretical free-fall height of 8.00 feet. Thus the difference in dropheights is only 0.74 feet. Now, a 1% error in the period measurement will be equivalent to a 2% error in the dropheight estimate, i.e. ±0.16 feet. But this represents a 22% error in the 0.74 foot difference.

On the other hand, if a smaller dropweight having an exact mass of 323 lbs. were to be dropped from a level of 4.67 feet, then the measured period would be about 14.30 milliseconds, which would correspond to 2.02 feet, or a difference in dropheights of 2.65 feet. Now a 1% error in the period measurement would be equivalent to a 2% error in the dropheight estimate (i.e. ±0.04 feet), and would result in only a 1.5% error in the 2.65 foot difference. Hence, the error in the determining of the energy measurement itself would be negligible.

The mathematical computations for the calculation of the theoretical height of drop which would yield the counted period in a free-fall situation are given below.

If a dropweight of weight "W" lb. is dropped from a height "H" ft. above a reference level, then $H = \frac{1}{2}gt_1^2$ where $g = 32.2$ ft./sec.$^2$ and $t_1$ is the time in seconds to fall this distance. If the dropweight on passing the reference level turns on a period measuring counter, and on passing a second reference level two inches below the first, turns off the counter, then we have a method of relating this time period, identified below as $\Delta t$ seconds, to the dropheight in feet, as follows:

$$H + \frac{2.000}{12} = \frac{1}{2} g(t_1 + \Delta t)^2$$

$$\text{or } t_1 + \Delta t = \sqrt{\frac{H + 0.166}{16.1}}$$

$$\text{but } t_1 = \sqrt{\frac{H}{16.1}}$$

$$\text{hence } \Delta t = \frac{1}{4.01}\left[\sqrt{H + .166} - \sqrt{H}\right]$$

The reference level in the apparatus illustrated in the figures is thus obviously related to the position of the dropweight 20 when the lowermost retro-reflective tape 57 has just initiated the beginning of the counting of the period. We may for convenience take the horizontal plane defined by the upper flat surface of the dropweight 20 as being our reference level at the time of this initiation of the period counting.

If we then take the measured period and calculate the value of H utilizing the above formulae, the resultant distance will be the difference between the top of the dropweight where it is actually located when the period counting begins and the theoretical location of the top of the dropweight in the position from which it would have to be released in order to produce the $\Delta t$ which we have counted.

Naturally, the true position from which the dropweight was in fact released would have been higher than this theoretically calculated position, due to the fact that a test-piece was in the way and was fractured by the dropweight 20. A calculation of the height difference between the top surface of the dropweight at the location from which it was actually released and the top surface of the dropweight at the theoretical calculated position will yield a length which, when multiplied by the actual weight or mass of the dropweight, will yield the true amount of energy absorbed by the test-piece in its fracture.

I claim:

1. Apparatus for determining the energy absorbed by an elongated test-piece of material during fracture thereof, comprising:

support means for supporting the test-piece during fracture including anvil means at either end of the test-piece;

a dropweight, vertical guide means for the dropweight, means for raising the dropweight along the guide means, and means for releasing the dropweight from a raised position directly above the test-piece to undergo substantial free-fall vertically after release, and means for measuring a determining characteristic of the motion of the dropweight after the test-piece has been fractured, the latter means including two retro-reflective areas affixed in vertically separated relation on the dropweight, a photoelectric beam projecting such that the retro-reflective areas pass sequentially into said beam, light-detecting means for sensing light reflected from said areas and for generating two time-separated electrical signals as the two areas pass sequentially into the beam, and electronic period-counter means to measure the time elapsing between the two electrical signals, the dropweight being an integral mass of metal shaped to define tow downwardly extending, laterally spaced-apart arms joined integrally together at the top thereby providing an internal slot extending upward from the bottom, the said guide means maintaining the dropweight in an orientation such that the test-piece is aligned with said internal slot, the dropweight including a striker bar supported horizontally across and at right-angles to said slot and said test-piece, whereby the striker bar contacts the test-piece substantially mid-way of each so that the fractured separated ends of the test-piece can pivot inwardly and into the slot above the striker bar, thus avoiding interference with the further downward free-fall of the dropweight.

and means directly beneath the initial test-piece location for catching and decelerating the dropweight after fracture of the test-piece.

* * * * *